US005633367A

United States Patent [19]
Kjell

[11] Patent Number: 5,633,367
[45] Date of Patent: May 27, 1997

[54] PROCESS FOR THE PREPARATION OF A 2-SUBSTITUTED 3,3-DIFLUOROFURAN

[75] Inventor: Douglas P. Kjell, West Lafayette, Ind.

[73] Assignee: Eli Lilly and Company, Indianapolis, Ind.

[21] Appl. No.: 410,258

[22] Filed: Mar. 24, 1995

[51] Int. Cl.$^6$ ................................ C07H 19/06
[52] U.S. Cl. ............ 536/28.5; 536/22.1; 536/28.3; 536/28.4; 536/28.51; 536/28.52; 536/28.53; 536/28.54; 549/429; 549/475
[58] Field of Search ............... 536/22.1, 28.3, 536/28.4, 28.5, 28.51, 28.52, 28.53, 28.54, 28.55; 549/429, 475

[56] References Cited

U.S. PATENT DOCUMENTS

| | | | |
|---|---|---|---|
| 4,526,988 | 7/1985 | Hertel | 549/313 |
| 4,808,614 | 2/1989 | Hertel | 514/45 |
| 4,921,950 | 5/1990 | Wilson | 536/23 |
| 4,965,374 | 10/1990 | Chou et al. | 549/313 |
| 5,047,520 | 9/1991 | Matsuda et al. | 536/23 |
| 5,223,608 | 6/1993 | Chou et al. | 536/28.5 |

FOREIGN PATENT DOCUMENTS

| | | | |
|---|---|---|---|
| 0 577 304 A1 | 1/1994 | European Pat. Off. | C07H 19/04 |
| 0 587 364 A1 | 3/1994 | European Pat. Off. | C07H 19/048 |

OTHER PUBLICATIONS

Chung et al., Chemical Abstract 122:187949, 1994.
Anas El–Laghdach et al., J. Org. Chem., 56, 4556–59 1991.
Anas El–Laghdach et al., Carbohydrate Research, 233, C1–C3, 1992.
Wilkinson, J.A., Chem. Rev., 92, 505–519 (1992).
Hudlicky, M., Fluorination with Diethylaminosulfur Trifluoride and Related Aminofluorosulfuranes, Organic Reactions, 35, 513–637, 1988.
Nishino, S., et al, Tetrahedron, 42(7), 1995–2004 (1986).
Andersson, F., et al., Carbohydrate Research, 129, C1–C3 (1984).
Ts'o, P.O.P., Basic Principles in Nucleic Acid Chemistry, Academic Press, New York and London, vol. 1, 177–190 (1974).
Bergstrom, D.E., et al., J. Med. Chem., 35, 3369–3372 (1992).
Sondej, S.C., et al., J. Org. Chem., 51, 3508–3513 (1986).
Sabol, J.S., et al., Tetrahedron Letters, 33, (22), 3101–3104 (1992).
Brodbeck, U., et al., J. Org. Chem., 35(10), 3552–3558 (1970).
Derwent Abstract 94–260509/32 of JP06192285 published Jul. 12, 1994.
Patrick, T.B., et al., Journal of Fluorine Chemistry, 25, 157–164 (1984).
Patrick, T.B., et al., J. Org. Chem., 46, 3917–3918 (1981).
Leroy, J., et al., J.C.S. Perkin I, 1224–1227 (1977).
Vyplel, H., et al., J. Fluorine Chemistry, 23, 482 (1983).
Ireland, R.E., et al., J. Org. Chem., 58, 2899 (1993).
Kondo, K., et al., J. Org. Chem., 42(17), 2809–2812 (1977).
Rozen, S., et al., American Chemical Society, 109, 896–897 (1987).
Antonakis, K., Advances in Carbohydrate Chemistry and Biochemistry, 42, 227–264, 1984.

Primary Examiner—Yogendra N. Gupta
Attorney, Agent, or Firm—Margaret M. Brumm; David E. Boone

[57] ABSTRACT

A process for the preparation of a 2-substituted-3,3-difluorofuran using diethyl ammonium sulfur trifluoride (DAST) and pyridine hydrogen fluoride. The process is particularly useful for producing a 2',2'-difluoronucleoside, particularly 1-(2',2'-difluoro-β-D-arabinofuranosyl)cytosine (also known as 2'-deoxy-2',2'-difluorocytidine), a known antiviral and antitumor agent.

6 Claims, No Drawings

PROCESS FOR THE PREPARATION OF A 2-SUBSTITUTED 3,3-DIFLUOROFURAN

BACKGROUND OF THE INVENTION

The present invention relates to a process for the preparation of a 2-position substituted-3,3-difluorofuran using diethylammonium sulfur trifluoride (DAST) reacted with a 2-position substituted furan-3-one. In particular the present invention relates to the preparation of a 2',2'-difluoronucleoside, particularly where the nucleobase is a pyrimidine such as cytosine.

A particular compound which is prepared by the process is 1-(2',2'-difluoro-β-D-arabinofuranosyl)cytosine (2',2'-difluorocytidine) from cytidine. This compound is an anti-cancer and antiviral agent.

A strategy for the synthesis of 1-(2',2'-difluoro-β-D-arabinofuranosyl)cytosine (2',2'-difluorocytidine) is the introduction of the 2',2'-difluoro groups into a suitably protected nucleoside precursor as shown in the following reaction Scheme 1.

Scheme 1

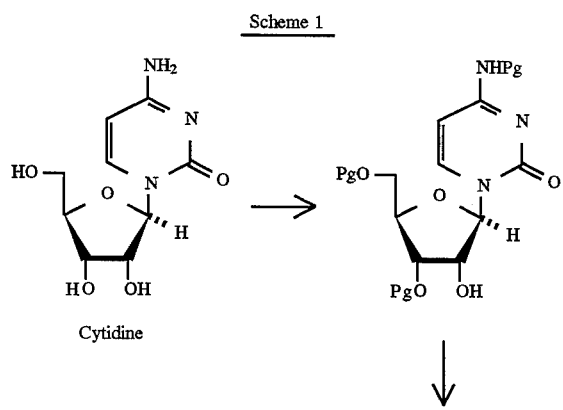

Cytidine

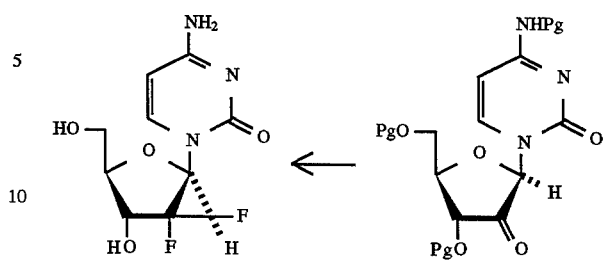

An economic analysis based on Scheme 1 shows that cytidine is a relatively inexpensive, commercially available starting material and thus Scheme 1 can be economically beneficial.

There are two primary issues associated with Scheme 1. The first of these is the development of an efficient protection scheme for cytidine that differentiates the 2'- and 3'-hydroxyl groups, and the provision of protecting groups (Pg) which survive a fluorination reaction. The second, more difficult problem is whether a suitably mild and selective process can be found for effecting geminal difluorination at C-2' of a 2'-ketonucleoside.

The peracylation, selective 2'-deacylation strategy reported by Nishino, et al., *Tetrahedron*, 42(7), 1995–2004 (1986) was successfully employed to address the protection-differentiation issue. The conversion of cytidine to the corresponding 2'-keto-3',5',N⁴-protected compound 3 was accomplished in three steps with an overall yield of 53% as outlined in reaction Scheme 2.

Scheme 2

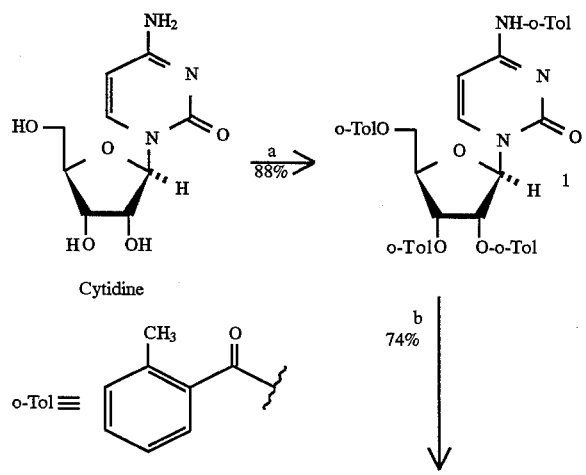

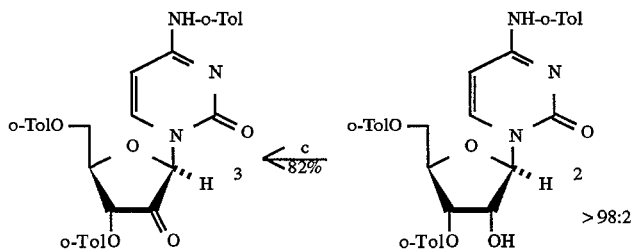

a. o-tol-Cl (5 eq), pyridine. b. KOt-Bu (4 eq), THF, −78° C. c. PDC (0.7 eq), Ac₂O (3 eq), CH₂Cl₂, 25° C. regiochemical purity by direct crystallization. It was found that the reported conditions (5 eq KOt-Bu, CH₂Cl₂, −20° C.) (Nishino, et al., *Tetrahedron*, 42, 1995–2004 (1986)) for the selective deacylation of compound 1 were unsatisfactory. However, under modified conditions (4 eq KOt-Bu, THF, −78° C., 1 hour) an 84:16 mixture of 2'- and 3'-deacylated nucleosides was obtained, respectively, from which the desired product, compound 2, was isolated in 74% yield and >98% purity.

Oxidation of 2 with PDC/Ac₂O (Andersson, et al., *Carbohydrate Res.*, 129, C1–C3 (1984)) gave the desired compound 3 in 82% yield.

The most convenient and direct method for the conversion of a carbonyl function into a gem difluoride is by treatment with one of the family of dialkylamino sulfur trifluoride reagents, of which the diethyl analog (DAST) is the most widely used example (Hudlicky, in "Organic Reactions", Wiley & Sons: New York, Vol. 35, Chapter 3, p. 513 (1988)). The reaction is shown in Scheme 3.

Scheme 3

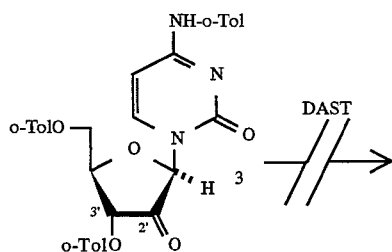

-continued
Scheme 3

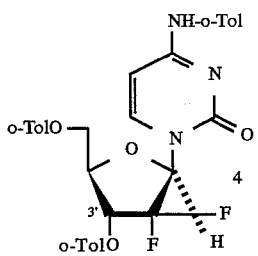

When compound 3 was treated with excess DAST in benzene at 25° C. for 70 hours most of the starting compound 3 was recovered intact. Under more forcing conditions, i.e. 80° C./16 hours or 110° C./16 hours, extensive degradation of compound 3 was observed. In none of these experiments was a significant amount (<0.5%) of the difluoride compound 4 detected. The reaction mixtures were assayed by reverse-phase HPLC after an aqueous workup.

In a related experiment, the 2'-hydroxy nucleoside 2 was treated with excess dimethylaminosulfur trifluoride at 25° C. (Scheme 4).

Scheme 4

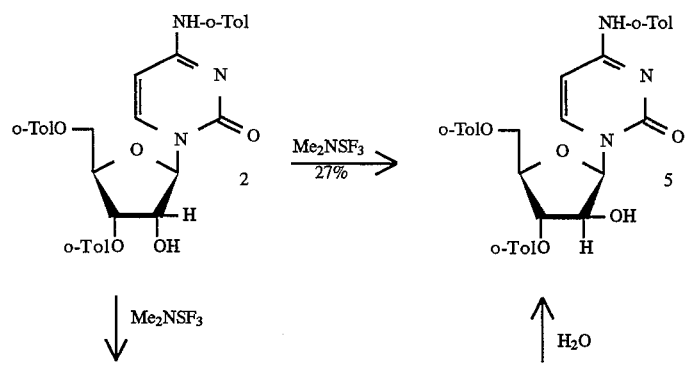

-continued
Scheme 4

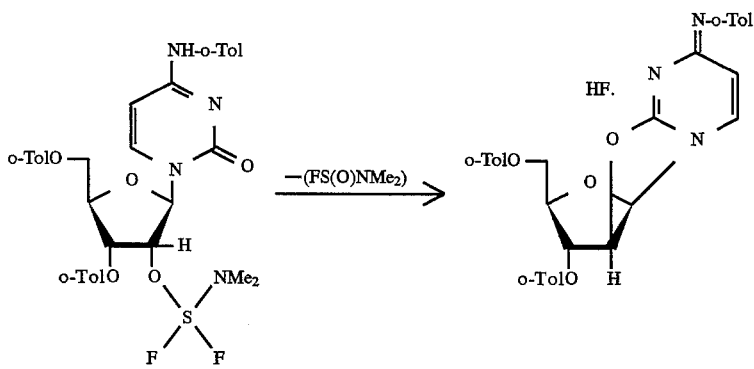

The only product that was identified in the resulting mixture was the corresponding ara-cytidine compound 5, which was isolated in 27% yield. The formation of this C-2'-inverted alcohol, instead of the corresponding 2',2'-difluoride, under these conditions strongly implicates the intermediacy of an $O^2$,2'-cyclonucleoside, which hydrolyzed to the derivative 5 on workup, as depicted in Scheme 4. The formation of such pyrimidine cyclonucleosides is well precedented, See: Goodman, L., in Basic Principles in Nucleic Acid Chemistry, Vol. 1; Ts'o, P. O. P., Ed.; Academic: New York, Chapter 2, pp 177–190 and references therein (1974)).

A related cyclonucleoside intermediate which could form on treatment of the 2'-keto compound 3 in Scheme 3 with DAST would regenerate the starting ketone during aqueous workup. After confirming the unreactivity of compound 3 toward DAST, and weakening the steric argument by the use of compound 3b shown in Scheme 5, the cause of the failure of the reaction was uncertain. One potential source of a failure to isolate products would be occurrence of the reaction shown in Scheme 5. DAST treatment results in formation of an internal geminal fluorohydrin ether. This molecule would decompose to starting material on aqueous workup, therefore no net reaction would be observed.

Scheme 5

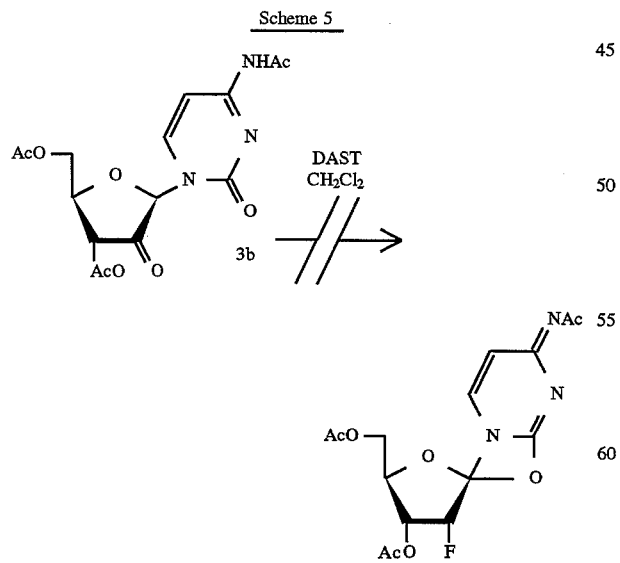

In the experiments, no evidence of the reaction in Scheme 5 was collected. The treatment of 3b with DAST was done in an NMR tube and monitored in situ. Formation of an intermediate which is stable until workup should have been observable. In fact, no shifts were observed in the proton NMR signals for molecule 3b which were not obscured by the DAST. Also, no species other than DAST was observed in the $^{19}$F-NMR.

Semi-empirical calculations were used to probe the reactivity differences between model compounds A and B and the 2'-keto compounds 3 and 3b. The difference between compound 3b and compounds A and B is shown by the Mulliken charge density at the oxygen:

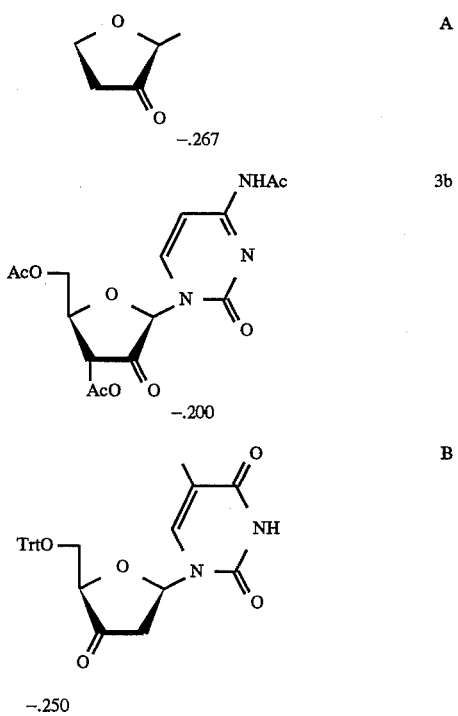

Molecule 3b possesses dramatically less charge density at the oxygen of the ketone. If a mechanism is assumed in which the first step of the fluorination is nucleophilic attack of this oxygen, then this lack of charge would explain the lack of reactivity. Further support of this theory was supplied by the difluorination of 3'-keto derivative B in the labs of Bergstrom, et al. (*J. Med. Chem.*, 35, 3369 (1992)). This molecule was calculated to have an electron density at oxygen similar to that of A.

7

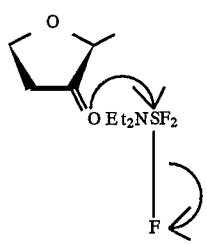

Another method for the conversion of a carbonyl compound to the corresponding 2',2'-difluorocytidine is the reaction of its derived dithioketal with BrF (Sondej, et al., *J. Org. Chem.*, 51, 3508–3513 (1986)). Despite numerous attempts, we were unable to effect the conversion of compound 3 to the requisite ethylene or propylene dithioketal intermediate compound 6 (Scheme 6).

Scheme 6

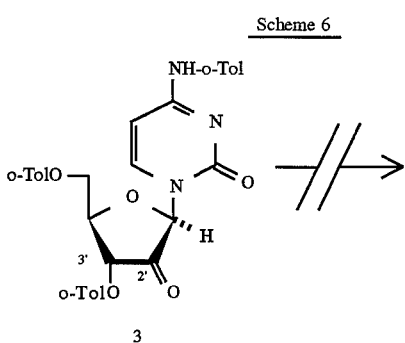

Treatment of compound 3 with ethane or propane dithiol at 25° C. in the presence of $BF_3$ etherate, $Zn(OTf)_2$, or $AlCl_3$ afforded no significant reaction. Under more forcing conditions, extensive degradation of compound 3 was observed. In no case was any of the desired product detected. Under two sets of conditions, ring cleavage products were isolated and identified (Schemes 7 and 8).

Scheme 7

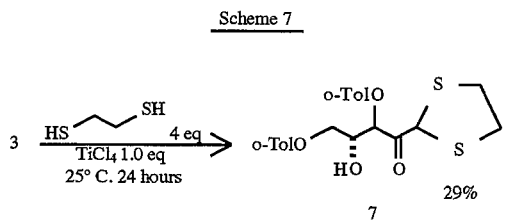

8

-continued
Scheme 8

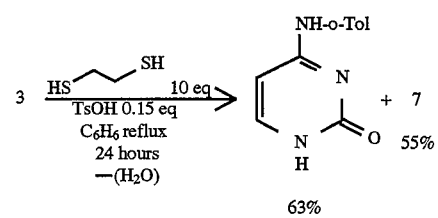

The formation of compound 7 under these conditions pointed to a serious selectivity problem and the process was abandoned.

There was a need for a fluorination process to prepare 2',2'-difluorocytidine from the corresponding 2'-ketocytidine. This process has potential for a much shorter and economical synthesis of 2-substituted-3,3-difluorofuran. The problem was to provide a process for performing the fluorination.

It is therefore an object of the present invention to provide a process for the fluorination of the 2-position substituted furan-3-one to produce a 2-position substituted-3,3-difluorofuran using DAST. The present invention particularly relates to a process for preparing 1-(2',2'-difluoro-3', 5'-di-O-acetyl-β-D-arabinofuranosyl)-$N^4$-acetylcytosine (2', 2'-difluorocytidine). Further, it is an object of the present invention to provide a process which provides the 2',2'-difluorocytidine in high yield. These and other objects will become increasingly apparent by reference to the following description.

DESCRIPTION OF PREFERRED EMBODIMENTS

The present invention relates to a process for the preparation of a 2-substituted-3,3-difluorofuran, the improvement which comprises reacting a 2-position X substituted furan-3-one with diethylammonium sulfur trifluoride (DAST) in the presence of a catalytic amount of pyridine hydrogen fluoride and in a non-reactive organic solvent at a temperature which produces the 2-substituted 3,3-difluorofuran, wherein X is a non-interfering, non-reactive substituent. Most preferred solvents are halogenated solvents such as methylene chloride and chloroform, and ethylene dichloride. Also preferred are nitriles such as acetonitrile.

Further the present invention relates to a process for the preparation of a 2',2'-difluoronucleoside which comprises reacting a 2-ketonucleoside of the formula

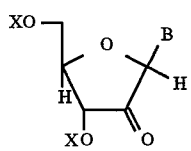

with diethylammonium sulfur trifluoride (DAST) in the presence of a catalytic amount of pyridine hydrofluoride and a non-reactive halogenated hydrocarbon solvent at a temperature which produces the 2',2'-difluoronucleoside, wherein X is a non-interfering, non-reactive substituent and B is a N-linked nucleobase.

The 2-position substituted furan-3-ones can have hydroxy groups which must be protected to keep them from reacting with the DAST, or being decomposed in some manner. Also, the 3'- and 5'-hydroxy groups of the nucleoside must be protected. These groups are chosen from the groups used in synthetic organic chemistry for the purpose. Chemists are accustomed to choosing groups which can be efficiently placed on hydroxy groups, and which can be easily removed when the reaction is complete. Suitable groups are described in standard textbooks, such as Chapter 3, of Protective Groups in Organic Chemistry, McOmie, Ed., Plenum Press, N.Y. (1972); and Chapter 2 of Protective Groups in Organic Synthesis, Greene, John Wiley & Sons, N.Y. (1981).

For example, hydroxlz-protecting groups include groups such as formyl, 2-chloroacetyl, benzyl, diphenylmethyl, triphenylmethyl, 4-nitrobenzyl, phenoxycarbonyl, t-butyl, methoxymethyl, tetrahydropyranyl, allyl, tetrahydrothienyl, 2-methoxyethoxymethyl, methoxyacetyl, phenoxyacetyl, isobutyryl, ethoxycarbonyl, benzyloxycarbonyl, and the like. Silyl groups cannot be used with DAST which removes these groups. A carbamoyl group can be used in the 3'- and 5'-position. Phenyl isocyanate ($R_1$=hydrogen, $R_2$=phenyl) can be used to prepare the carbamoyl derivatives. Analogous derivatives are produced from diphenyl carbamoyl chloride ($R_1$=$R_2$=phenyl), dimethyl carbamoyl chloride ($R_1$=$R_2$=methyl), nitrophenyl isocyanate ($R_1$=hydrogen, $R_2$=nitrophenyl) and the like. The phenyl or alkyl moieties can be substituted with various non-reactive groups.

The pyrimidine nucleobases employed herein for the B group of the nucleoside are commonly known to organic chemists and no discussion of their synthesis is necessary. However, in order to be useful in the present process the nucleobases or their tautomeric equivalents, bearing amino or hydroxy groups preferably contain primary amino protecting groups (W) and/or hydroxy protecting groups (Z), depending on the nature of the nucleobase derivative selected. The protecting group blocks the hydroxy or amino groups which may provide a competing reaction site. The protecting groups are attached to the nucleobase derivative before it is reacted with the DAST of the present invention and are removed subsequent thereto. A procedure for protecting the nucleobase derivatives is described in U.S. Pat. No. 4,526,988 to Hertel.

Preferred amino protecting groups (W) for pyrimidine nucleobase derivatives are selected from the group consisting of carbamates such as t-butoxycarbonyl, benzyloxycarbonyl, 4-methoxybenzyloxycarbonyl, and 4-nitrobenzyloxycarbonyl, formyl, acetyl and benzoyl; ether forming groups such as methoxymethyl, t-butyl, benzyl, allyl and tetrahydropyranyt. Preferred hydroxy protecting groups (Z) for pyrimidine nucleobase derivatives are selected from carbocyclic esters such as formyl, acetyl, and pivaloyl.

Thus B is a nucleobase selected from the group consisting of

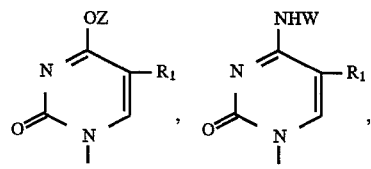

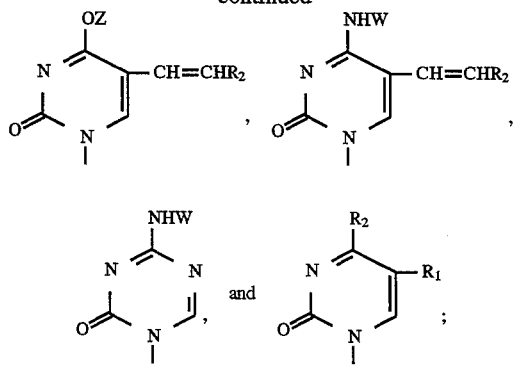

wherein $R_1$ is selected from the group consisting of hydrogen, alkyl, substituted alkyl and halo; $R_2$ is selected from the group consisting of hydrogen, alkyl and halo; Z is a hydroxy protecting group and W is an amino protecting group.

In providing protectable groups for the nucleobase, the protecting group itself may be protected.

In addition, it is often advisable to convert keto oxygen atoms on the nucleobase to an enol form. This makes the nucleobase derivative more aromatic and enhances the reactivity of the nucleobase derivative. It is most convenient to enolize the keto oxygens and provide protecting groups for them. In a preferred embodiment of the present process the nucleobase derivative is of the formula

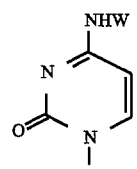

wherein W is acetyl.

For instance as shown in Example 5, the compound 1-(2',2'-difluoro-β-D-arabinofuranosyl)cytosine (10) can be prepared by fluorination of a 2'-ketocytidine (1-(2'-keto-3', 5'-di-O-acetyl-β-D-arabinofuranosyl)-$N^4$-acetytcytosine (8) to produce 1-(2',2'-difluoro-3',5'-di-O-acetyl-β-D-arabinofuranosyl)-$N^4$-acetylcytosine (9) by the reaction shown below in Scheme 9.

Scheme 9

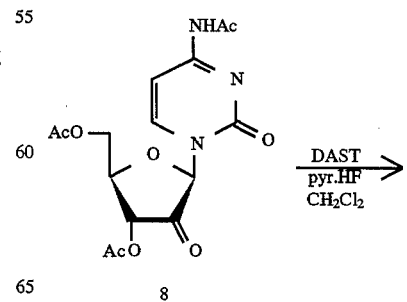

-continued
Scheme 9

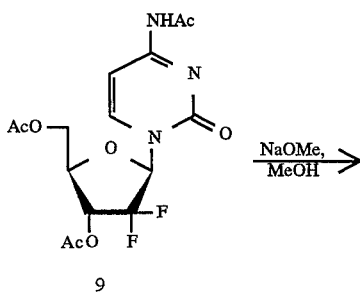

The addition of pyridine hydrofluoride to DAST (diethylammonium sulfur trifluoride) unexpectedly allowed the reaction to proceed to completion. Other protecting groups can be used for the 3' and 5' and $N^4$ positions. This invention allows a small number of synthesis steps to produce 1-(2',2'-difluoro-β-D-arabinofuranosyl)cytosine. The same process is used to make other 2',2'-difluoro nucleosides or furan-3-ones.

EXAMPLE 1

Scheme 10

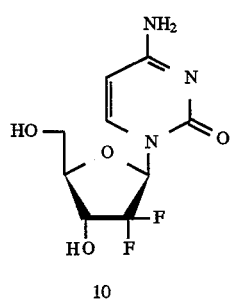

This experiment was designed to show the unique catalytic effect of pyridine-HF. The reactions below were not optimized, nor were they run to completion.

In a 25 mL graduate were combined 2-methyltetrahydrofuran-3-one (11) (0.47 mL, 10 mmol), anisole (1.0 mL, as intl std, Aldrich) and acetonitrile ($CH_3CN$) (Q.S. to 20 mL) to provide a reaction mixture.

DAST (2.64 mL, 20 mmol) was added to the reaction mixture. The mixture was then split into four parts.

Nothing was added to portion A. To portion B was added: potassium triflate (0.26 g, 1.5 mmol). To portion C was added: potassium fluoride (0.09 g, 1.5 mmol). To portion D was added: pyridine-HF (ca. 100 μl, Aldrich).

The reaction mixtures were sampled periodically and analyzed by GC. The catalytic effect of pyridine hydrogen fluoride was clearly apparent. For instance, after 180 minutes part D showed approximately twice the yield of the control A (23% vs. 12.5%). Reaction C was not distinguishable from the control. No reaction occurred in portion B.

EXAMPLE 2

This experiment was designed to show the catalytic effect of pyridine-HF. The reaction is diluted to slow the uncatalyzed reaction, so the effect can be seen.

In a 25 mL graduate was added 2-methyltetrahydrofuran-3-one (11) (0.97 mL, 10 mmol), anisole (1 mL, as an internal standard, Aldrich) and dichloromethane (Q.S. to 20 mL) to form a reaction mixture.

DAST (2.64 mL, 20 mmol) was added to the reaction mixture. The reaction mixture was divided into 4 parts. Table 1 shows what was added to the reaction mixture.

TABLE 1

|  | A | B | C | D |
| --- | --- | --- | --- | --- |
| HF Pyridine (Aldrich) (~70% HF) | 0 | 14 μL | 70 μL | 140 μL |
| mmol HF | 0 | ~0.5 mmol | 2.5 mmol | 5 mmol |

The reaction mixtures were sampled periodically and analyzed by G.C. After 120 minutes, a 25% yield of 3,3-difluorohydrofuran 12 was obtained without catalyst (Example A). The catalyzed conditions showed optimum yield in Example C (45%). Example B had a lower yield (40%) due to incomplete reaction. Example D (40%) had a lower yield due to decomposition.

EXAMPLE 3

Scheme 11

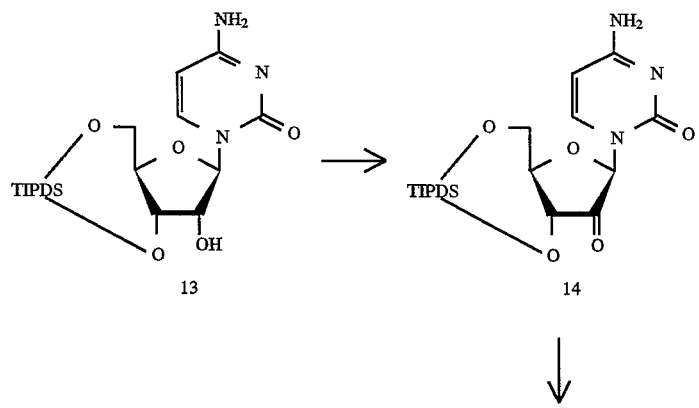

-continued
Scheme 11

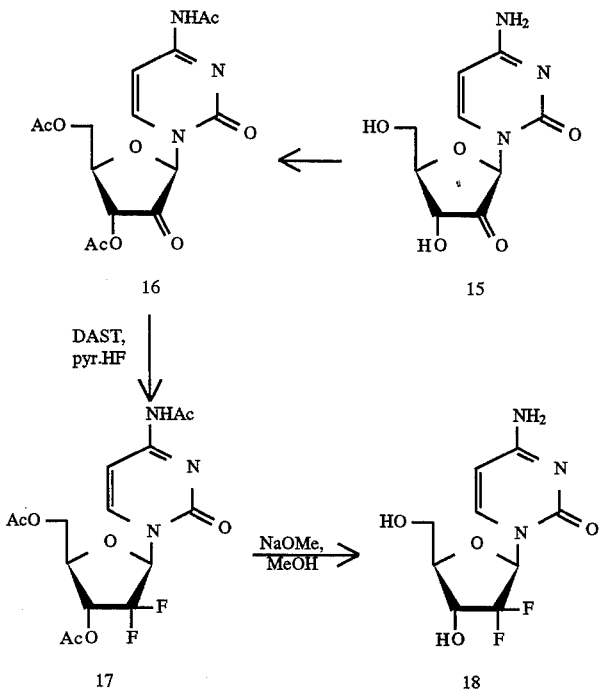

As shown in Scheme 11, the 3' and 5' positions are protected with TIPDS, a 3',5'-O-tetraisopropyl-disoloxane-1,3-diyl group (see Sabol, et al., *Tet. Letters*, 33(22), 3101–3104 (1992)).

To a 25 mL round bottom flask with magnetic stirring under nitrogen was added: 3',5'-TIPDS cytidine 13 (600 mg, 12 mmol, Aldrich), dimethylsulfoxide (6 mL), and acetic anhydride (0.60 mL). The reaction was stirred 4 hours (TLC indicated complete reaction). The mixture was partitioned between ethyl acetate and water. The organic layer was washed twice with water, then once with brine, then dried over magnesium sulfate. The solution was evaporated to yield 2'-keto-3',5'-TIPDS cytidine (14).

To the unpurified TIPDS cytidine 14 was added 1 molar tetrabutylammonium hydroxide in THF (9 mL). After the reaction was complete by TLC, the mixture was concentrated in vacuo to a residue. The residue was taken up in ethyl acetate (30 mL), and dried over $MgSO_4$. The mixture was evaporated again to yield the unprotected 2'-ketocytidine (15).

To the unpurified ketocytidine (15) were added ethyl acetate (9 mL), acetyl chloride (0.51 mL, 7.2 mmol), and triethylamine (1.03 mL, 7.2 mmol). The mixture was stirred overnight. The resulting solution was washed with water, dried over $MgSO_4$, and evaporated in vacuo to yield $N^4$,3', 5'-triacetylcytidine (16).

To the $N^4$,3',5'-triacetylcytidine (16) (0.2 g) prepared above were added dichloromethane (1.0 mL), DAST (0.1 mL), and pyridine.HF (ca. 60 µL) The mixture was stirred 2 days, then stripped to yield $N^4$,3',5'-triacetylgemcitabine (17).

Deprotection by reaction with sodium methoxide in methanol yielded 2'-deoxy-2',2'-difluorocytidine (18).

EXAMPLE 4

When the procedure of Example 3 was repeated without pyridine hydrogen fluoride. No compound (17) was formed. Thus, the procedure of Bergstrom, et al., *J. Med. Chem.*, 35, 3369–3372 (1992) was not effective in producing compound (17).

EXAMPLE 5

Formation of gemcitabine from $N^4$,3',5'-tri(o-toluoyl)-2'-ketocytidine (3).

$N^4$,3',5'-tri(o-toluoyl)-2'-ketocytidine 3 (Scheme 3) (0.30 g, 0.5 mmol), dichloromethane (1 mL), DAST (1.3 mL, 10 mmol, Aldrich), and pyridine.HF (50 µL) were combined in a 10 mL round bottom equipped with magnetic stirring. The flask was sealed and stirred for 24 hours. After 24 hours HPLC suggested 80% reaction. The mixture was diluted with dichloromethane (50 mL). The resulting solution was washed three times with water (3×25 mL), saturated sodium bicarbonate (50 mL), and brine (50 mL). The organic phase was dried over $MgSO_4$. Rotary evaporation gave 0.13 g of a solid. HPLC, $^1$H-NMR, and $^{13}$C-NMR were consistent with the solid being 80% the desired 2',2'-difluoro derivative 4 (Scheme 3), and 20% residual 3. The solid was dissolved in methanol (2 mL) and treated with sodium (ca. 50 mg). After 15 minutes HPLC analysis confirmed the formation of 2',2'-difluorocytidine 18 (Scheme 11).

It is intended that the foregoing description be only illustrative of the present invention and that the present invention be limited only by the hereinafter appended claims.

I claim:

1. A process for the preparation of a 2',2'-difluoronucleoside which comprises:

reacting a 2-ketonucleoside of the formula

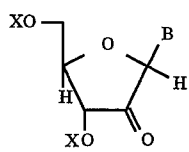

with diethylammonium sulfur trifluoride (DAST) in the presence of a catalytic amount of pyridine hydrofluoride and a non-reactive halogenated hydrocarbon solvent at a temperature which produces the 2',2'-difluoronucleoside, wherein x is a non-interfering, non-reactive hydroxy protectinq group selected from the group consisting of acetyl, formyl, 2-chloroacetyl, benzyl, diphenylmethyl, triphenylmethyl, 4-nitrobenzyl, phenoxycarbonyl, t-butyl, methoxymethyl, tetra-hydropyranyl, allyl, tetrahydrothienyl, 2-methoxyethoxymethyl, methoxyacetyl, phenoxyacetyl, isobutyryl, ethoxycarbonyl, end benzyloxycarbonyl, and B is a N-linked nucleobase.

2. The process of claim 1 wherein the nucleobase is selected from the group consisting of

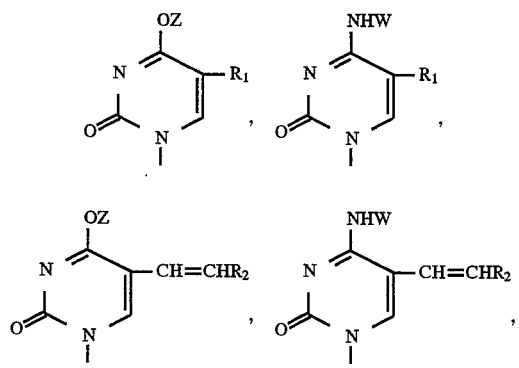

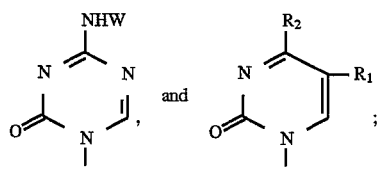

wherein $R_1$ is selected from the group consisting of hydrogen, alkyl, substituted alkyl and halo; $R_2$ is selected from the group consisting of hydrogen, alkyl and halo; Z is a hydroxy protecting group and W is an amino protecting group.

3. The process of claim 2 wherein the N-linked nucleobase is

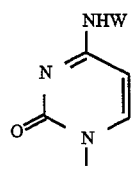

wherein W is an amino-protecting group.

4. The process of claim 3 wherein W and each X is acetyl.

5. The process of claim 1 wherein the temperature is between about 0° C. and 30° C.

6. The process of claim 1 wherein the solvent is dichloromethane.

* * * * *